United States Patent [19]

Diamond

[11] Patent Number: 5,337,741

[45] Date of Patent: Aug. 16, 1994

[54] PHOTO RADIATION TREATMENT APPARATUS AND METHOD

[76] Inventor: Donald A. Diamond, 5416 Harbor Rd., Bradenton, Fla. 34209-1832

[21] Appl. No.: 718,615

[22] Filed: Jun. 21, 1991

[51] Int. Cl.$^5$ .............................. A61N 5/06
[52] U.S. Cl. ........................... 600/8; 606/11; 606/13; 606/17; 606/10
[58] Field of Search ............... 128/395-398, 128/898; 606/2, 3, 8-13, 16, 17; 604/23

[56] References Cited

U.S. PATENT DOCUMENTS

| | | | |
|---|---|---|---|
| 3,867,948 | 2/1975 | Kallenborn | 128/395 |
| 3,930,504 | 1/1976 | Laforcade | 606/11 X |
| 4,388,924 | 6/1983 | Weissman et al. | 606/17 X |
| 4,628,416 | 12/1986 | Dewey | 606/17 X |
| 4,791,927 | 12/1988 | Menger | 606/10 X |
| 4,931,053 | 6/1990 | L'Esperance, Jr. | 606/10 X |
| 5,019,074 | 5/1991 | Muller | 606/13 X |
| 5,071,417 | 12/1991 | Sinofsky | 606/10 X |

OTHER PUBLICATIONS

The Merck Manual of Diagnosis and Therapy, Fifteenth Ed. Merck Sharp & Dohme Research Lab, pp. 1239-1247, 1987.

Primary Examiner—Peter A. Aschenbrenner
Attorney, Agent, or Firm—Allen, Dyer, Doppelt, Franjola & Milbrath

[57] ABSTRACT

An apparatus for radiating high intensity energy at a subject for treating diseases such as rheumatoid or psoriatic arthritis and a method for using the same. A radiation source generating radiation at a predetermined output wavelength transilluminates affected tissues of the subject for a predetermined duration. The radiation source has sufficient intensity and is applied for sufficient duration to photolyze disease-specific antigens within the transilluminated tissues responsible for evoking complex immune response, thus reducing inflammation and disease progression.

4 Claims, 1 Drawing Sheet

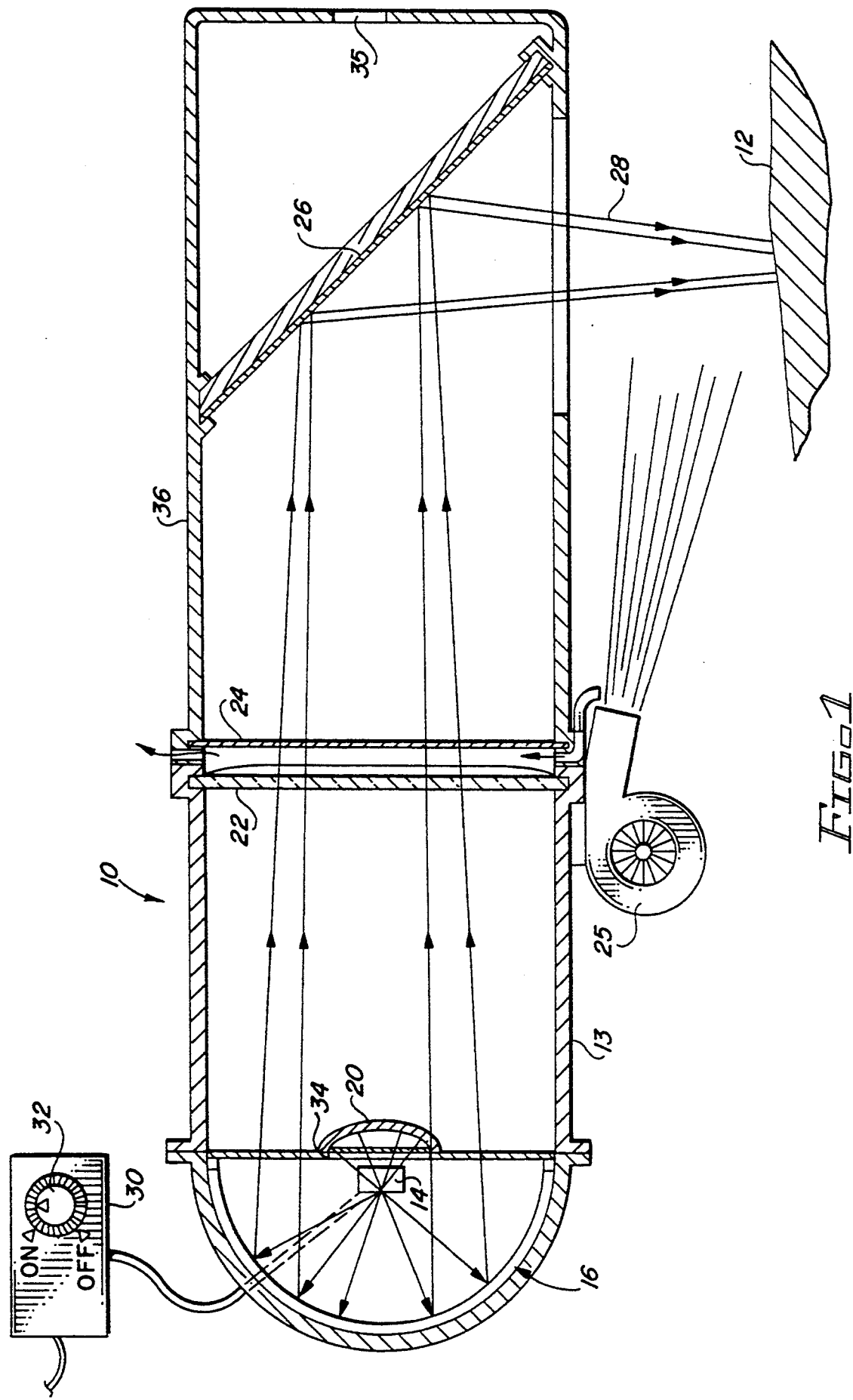

PHOTO RADIATION TREATMENT APPARATUS AND METHOD

BACKGROUND OF THE INVENTION

This invention relates to apparatus and methods for therapeutic intervention of the complex immune response in rheumatoid and psoriatic arthritis. More specifically, this invention relates to the treatment of arthritis by transilluminating electromagnetic radiation having a predetermined bandwidth and power density to photolyze the antigen evoking the complex immune response.

The correlation of palliation of the symptoms of rheumatoid arthritis with a subject's exposure to direct sunlight has been well established for more than a century, as has seasonal severity of flare-ups of the disease syndrome. These data suggest a photoreactive mechanism is involved.

Many devices which generate and project radiation transcutaneously have been used to treat arthritics, such as diathermy and laser devices. The transient anti-inflammatory action of induced hyperthermia is well-established. Examples of these devices are disclosed in German Patent No. DE 3103731 A1 and Soviet Union Patent Publications SET 993959 and SU 741889. SU 993959 discloses introducing the antibiotic tetracycline into the subject's interarticular space and then irradiating the joint with a helium-neon laser for two to four minutes. SU 741889 discloses introducing dye material into the joint cavity and then applying a 488 nm argon laser to the joint for five minutes. These techniques are palliative, but do not suggest a permanent remission of the disease, or sustained action in arresting the progression of the disease. Further, these techniques require invasive procedures and hypodermic introduction of materials.

Other methods of providing palliation of arthritic symptoms are disclosed in Soviet Union Patent Publications SU 1266540 and SU 1142125A. These methods deliver thermal energy to the inflamed joint. Again, these methods make no claim to prolonged remission or arrest of disease progression.

SUMMARY OF THE INVENTION

An objective of this invention is to provide an improved therapeutic modality for treating rheumatoid and psoriatic arthritis.

A further objective of this invention is to arrest progressive degeneration caused by rheumatoid and psoriatic arthritis with a device that photolyses an antigen with high intensity electromagnetic radiation of a specific bandwidth.

Another objective of the invention is to attenuate the body's complex immune response to antigens migrating through the synovial membrane and infiltrating adjacent soft tissues by transilluminating these structures with electromagnetic radiation having an effective bandwidth of 640–800 nanometers wavelength, and photolyzing the antigen.

An additional objective of the invention is to reduce pain, inflammation and fluid retention symptoms characterizing arthritis.

An additional objective of the invention is to provide a prolonged reduction in the titer of the antigen disposed in the synovial fluid and adjacent tissues such that by using the therapeutic technique, symptomatic relief of the disease may be extended for some months or years.

These and other objectives are accomplished by the use of an apparatus and a technique for treating rheumatoid and psoriatic arthritis in the body of a subject. The method includes the following steps:

1. A radiation source of adjustable intensity having an output bandwidth of 640–800 nanometers wavelength with a converging beam is provided.
2. The entry ports, such as the epidermis adjacent the subject's target joint, are coated with mineral oil to facilitate penetration and minimize scattering of the beam.
3. A low velocity air flow is directed to the epidermis of the subject adjacent the target joint to dissipate superficial heat and avoid thermal damage to the epidermis.
4. The incident power of the radiation source is set between 40 and 200 milliwatts per square centimeter for an exposure time of up to twenty minutes, but not exceeding 100 joules per centimeter squared. The duration and intensity is selected to photolyse antigens throughout the inflamed tissue.
5. The apparatus is adjusted so that the beam is directed at the target joint of the subject at port angles which facilitates the transillumination of the synovial fluid and the prescribed dosage is administered. The power density may be reduced at any time to avoid discomfort so long as the prescribed total joules dose is administered by extending exposure time proportionately.

Clinical studies to date indicate that an uncorrelated transient reduction of pain is experienced in nearly all subjects, attributed to local hyperthermia, with a typical duration of three to six hours. In a positive response, occurring within some 84% of the tested population, the symptomatic indications of inflammatory process subside within 12 to 48 hours following treatment, and recurrence of symptoms are manifest between ten to sixteen months in over 80% of the subjects. All subjects were medically diagnosed with rheumatoid arthritis, but not all subjects titered positive for rheumatoid immunoglobulin. It is therefore posited that some other disease entity may have been responsible for the patient's failure to respond in the remaining 16% of the tested population. One subject had no recurrence of symptoms after 47 months without pharmacologic intervention. This subject had completed a course of prednisone and ibuprofen for 14 months prior to treatment and had an 18-year history of rheumatoid arthritis at that time.

It is posited that rheumatoid arthritis is a vertically-transmitted congenital disease, which pathogenic agent is an opportunistically replicating, photolyzable viroid, having an estimated size of 8 nanometers by 720 nanometers. When synovial fluid is extracted and exposed to ambient light in clinical or laboratory settings, the viroid photolyzes RNA fragments to a size less than 200 nanometers in length, which fragments resemble cell debris.

It is believed that arthritic inflammation is caused by the subject's immune response to the viroid Thus, by fracturing the viroid, the body's immune response subsides and symptomatic remission is obtained. Joint erosion, cartilage loss, and other degenerative aspects are attributed to chronic inflammation, and not directly to viroid insult.

BRIEF DESCRIPTION OF THE DRAWING

FIG. 1 is a sectioned view of the treatment device for directing the electromagnetic beam at the afflicted joint provided with an excited tungsten source for generating electromagnetic radiation of the appropriate bandwidth and intensity.

DESCRIPTION OF THE PREFERRED EMBODIMENTS

Referring to FIG. 1, there is shown the apparatus 10 for irradiating high intensity electromagnetic radiation at the epidermis 12 on the body of a subject to reduce arthritic inflammation. The device includes a housing 13 having a sealed radiation source 14 sinking up to 600 watts from a 0–28 volt D.C. power supply 30. The radiation source 14 is a sealed-beam tungsten aircraft landing light within housing 13. One such sealed-beam tungsten source is Westinghouse model no. 4559, distributed by Jones Aviation Corp. of Sarasota, Fla.

The radiation source 14 preferably has a tungsten filament and a parabolic reflector. The output wavelength of source 14 is between 350 and 10,000 nanometers (nm) and is directed at radius mirror 20 and affixed to the face of the sealed-beam assembly. Radius mirror 20 reflects radiation emitted by the tungsten filament back to parabolic reflector to enhance collimation by eclipsing the direct beam. Although a tungsten source is preferred, any source that provides beams in the range of at least 640–800 nm with at least a two-watt power output may be used. The output of the source 14 is a substantially collimated radiation beam which projects to fresnel lens 22. Fresnel lens 22 converges the substantially collimated radiation through primary gel filter 24. The converged radiation is then reflected off mirror 26, out aperture 28 and onto the arthritic joint of the subject.

Radius mirror 20 is preferably coated with an AL-SiO surface. Radius mirror 20 manufactured by Edmond Scientific of Barrington, N.J. preferably has a focal length of 100 millimeters and a 50 millimeter diameter mounted with an optical adhesive 34. Adhesive 34, manufactured by Norland Optical of New Brunswick, N.J., is preferably edge sealed on the radius mirror's outer surface, which is attached to the center of the sealed beam face.

Tungsten radiation source 14 is powered by power supply 30. Power supply 30 is enabled, adjusted, and disabled by switch potentiometer 32. Preferably, power supply 30 provides an adjustable 0–28 volts to radiation source 14 to change the radiation intensity.

Fresnel lens 22 converges the collimated radiation from radiation source 14. Fresnel lens 22 is preferably constructed with acetate butyrate having a thickness of 2.8 millimeters, a 203 millimeter active diameter, and a focal length of 46 cm with a 92% transmission. One such lens is model no. R43015 distributed by Edmund Scientific of Barrington, N.J. The converged output of fresnel lens 22 is fed through primary gel filter 24 which preferably has a peak pass of 88% transmission at a wavelength of 710 nanometers and 50% transmission at wavelengths of 635 and 775 nanometers. One such primary filter material is film no. 823, manufactured by Rosco Laboratories, Inc. of Port Chester, N.Y. A blower 25 directs air between lens 22 and filter 24, as well as at the subject, to dissipate superficial heat, preventing thermal damage to the epidermis.

A mirror 26 is affixedly coupled to housing 13 with bracket 36. The converged radiation is reflected off cold mirror 26 at aperture 28. A portion of the converged radiation having a wavelength greater than 800 nm passes through mirror 26 and aperture 35 at a far end of housing 13. A heat sink may be positioned in aperture 35 to absorb radiation passing through mirror 26. Approximately 10% of the radiation is absorbed by mirror 26. Mirror 26 is preferably model no. F42414 distributed by Edmond Scientific of Barrington, N.J.

Preferably the total beam power is adjustable from 0 to 9.37 watts to a target size on epidermis 12 of seven to seventy square centimeters for a range of power density of 0 to 1340 milliwatts per centimeter squared. Practical dose levels of 90 joules per centimeter square are accomplished with power levels of 75 milliwatts per centimeter square over a twenty minute exposure interval.

It is preferable that, during an application of the output radiation on the subject, a radiation beam of 40 to 200 milliwatts per square centimeter radiates onto the arthritic joint for a period of about twenty minutes. It is also preferable that the wavelength of this output radiation be set between 640 and 800 nanometers for optimum results.

It has been found through experimentation that a positive response can be defined as significant reduction or remission of pain and inflammation for more than four months; this response has been demonstrated in 84% of the subjects. Apparently, disease progression is arrested in the interval of remissions.

Reference is made to the following examples of radiation treatment:

EXAMPLE 1

Subject is a 50 year old white male having rh immunoglobulin positive for four years and was symptomatic for 17 years. The principal source of inflammation was in the symmetrical proximal carpals and metacarpals and phalanges-metatarsals.

The subject was initially dosed with 200 joules on the palmar and dorsal right first metacarpus. On the following day the subject reported a remission of inflammation with a return of range of motion of the irradiated joints without pain.

Three days later 200 joules were irradiated at the palmar and dorsal as well as the left first metacarpus. A remission of inflammation was recorded the following day with a return of normal range of motion without pain of the irradiated joints.

The next day the palmar and dorsal surfaces were irradiated as well as the left second metacarpal and left proximal phalange with 100 joules. The following day the subject reported a reduction of inflammation and pain of the irradiated joints.

Two days later the subject was irradiated with 200 joules on the palmar and dorsal, the left second metacarpal and the left second proximal phalange. The subject experienced remission of inflammation the following day.

The next day the subject was irradiated with 200 joules palmar and dorsal on the remaining metacarpals and phalanges. The subject experienced overnight remission of inflammation and pain.

One month later the right plantar and dorsal metatarsals and proximal phalanges were irradiated with 1200 joules on each surface for a total of 4800 joules The subject experienced a remission of inflammation and pain.

On the following day the left plantar and dorsal and metatarsals, and proximal phalanges were radiated with 1000 joules on each surface for a total of 4000 joules. A remission of inflammation and pain was reported by the subject.

Approximately one year later the subject reported symmetrical recurrence of pain and inflammation in the first metacarpals. The subject was irradiated on the metacarpals and proximal phalanges en bloc for a total of 6000 joules. Subject reported a positive response as there was a remission of inflammation and pain.

A year and a half later the subject reported symmetrical recurrence of pain and inflammation in metatarsals. The subject was irradiated on the metatarsals on proximal phalanges, as well as the left plantar and dorsal, with a dosage of 1000 joules on each surface. Subject reported a remission of inflammation and pain. Subject has not reported a recurrence as of date.

EXAMPLE 2

The subject is a twenty-year old white male having ra immunoglobulin positive for 18 years prior. The inflammation on the subject was limited to tarsals and metatarsals on the right foot. The subject was irradiated on the right foot with 6000 joules total. The subject reported overnight remission of inflammation and pain. Annual follow-ups relate continuing remission of symptoms as of date four years later.

EXAMPLE 3

The subject is a thirty-nine year old black female experiencing ra immunoglobulin positive for the past nine years. The left scapula, left femoral head and pelvis were irradiated with a dosage of 2400 joules each. Subject experienced a positive response where the inflammation and pain were remitted.

Four days later the left humerus head, right and left tarsus, first wrist and second and third metacarpals were irradiated with 2000 joules, 2400 joules, and 1400 joules, respectively. The subject experienced a positive response where a remission of inflammation and pain were recorded.

A year and a quarter later the subject reported recurrence in the left hip. The subject is treated with irradiation on the left scapula, left femoral head and pelvis. The dosage of the radiation was increased to 4800 joules and the subject experienced a positive response. In this response the pain and the inflammation were decreased.

One year later the subject reported no recurrence.

EXAMPLE 4

The subject is a twenty-year old white male, experiencing ankylosing spondylitis. A dosage of 2400 joules was applied to the lumbar-sacral spine. No response was obtained.

In this instance, it was demonstrated that ankylosing spondylitis was not arrested with radiation. This example also implies rheumatoid arthritis is arrested due to photolyzing antigens, and not due to thermal effects.

EXAMPLE 5

The subject is a four-year old juvenile with arthritic symptoms in the right tarsus. Two doses at four day intervals at 900 joules were applied to the subject's right tarsus. The subject did not respond to the irradiation application.

This example suggests that juvenile arthritis is not the same disease entity as adult rheumatoid arthritis.

EXAMPLE 6

A subject having osteoarthritis, age sixty, in the distal phalanges. A dosage of 400 joules was applied to the phalanges. Subject did not respond to this application.

This example demonstrated that osteoarthritis is a disease entity of differing causality. This example also demonstrated that treating osteoarthritis by transilluminating electromagnetic radiation does not provide long-term reduction of pain and inflammation.

EXAMPLE 7

A sixty-two year old female having rheumatoid arthritis on the wrists and the hands was irradiated en bloc in four exposures. The palmar and ventral surfaces were irradiated with a dosage of 2400 joules each. The subject experienced a positive response in metacarpals and a partial response in wrists.

Less than one month later the wrists of the subject were irradiated with 3000 joules. The subject had a positive response, a reduction of pain and inflammation.

Less than two months later the subject was observed and a symptomatic recurrence was reported. The subject was retreated with a 3000 joules application. A positive response was reported by the subject with a reduction in pain and inflammation.

EXAMPLE 8

The subject is a fifty-four year old male and was diagnosed as rheumatoid in the knuckles, shoulders, elbows, knees, ankles and toes.

The subject was treated on the knuckles of the right hand with a thirty minute exposure. The subject had no pain or stiffness by the following morning, although inflammation was still present in the hands.

One week later the knuckles of the left hand were exposed for approximately 15 minutes on each side, and the toes of the right foot were also exposed for 15 minutes. The dosage applied was 1800 joules.

The following morning the subject experienced no pain or stiffness in the right foot while the subject's untreated left foot was throbbing. The subject did not experience any pain but did have some stiffness in the untreated left hand. The previously treated right hand felt normal with no discomfort of any kind. Subject did experience pain and swelling for a few days after heavy impact to the right hand during physical activity with a target pistol.

Three weeks later the subject's knuckles of the right hand were treated and two weeks following that treatment, the knuckles of the left hand as well as the toes of the right foot were treated. In both cases the subject was treated for a duration of twenty minutes at a dosage rate of 1800 joules.

One month later all the areas that were treated were normal. Subject did not experience stiffness or discomfort.

Two months after the last treatment the subject was exposed on his heel of the right foot for approximately twenty minutes with a dosage level of 1800 joules. Subject experienced an immediate relief of pain. The following day the subject experienced less pain with no stiffness in the right heel. Knuckles in the right hand, treated the previous month, felt normal with no discomfort of any kind, and the knuckles of the left hand and toes of the right foot, treated two months previously, felt normal with no discomfort of any kind.

Although not completely understood, this photon wavelength directed to the inflamed tissue is believed to photolyze viroids within the soft tissue. It is believed that photolyzing these viroids (the antigen responsible for the complex immune response), results in a reduction in arthritic inflammation. It is preferable that the epidermis 12 incident to the photon beam be coated with mineral oil prior to directing the radiation source at the epidermis 12 of the subject. The mineral oil enhances subcutaneous transmission of the beam, permitting more energy to be delivered to deep tissues.

This concludes the description of the preferred embodiments. A reading by those skilled in the art will bring to mind various changes without departing from the spirit and scope of the invention. It is intended, however, that the invention only be limited by the following appended claims.

What is claimed is:

1. A method of treating rheumatoid and psoriatic arthritic inflammation on the body of a subject, the method comprising the steps of:
   providing a radiation source having an output wavelength bandwidth between 640 nanometers and 800 nanometers; and
   irradiation said output at the epidermis of the subject to transilluminate the arthritic joint with an incident power in the range of 40 to 200 milliwatts per square centimeter for a time sufficient to provide an effective treatment.

2. The method of treating arthritic inflammation as recited in claim 1 further comprising the step of facilitating penetration of the radiation by coating the target epidermis with mineral oil prior to directing the radiation source at the subject.

3. The method of treating arthritic inflammation as recited in claim 1 further comprising the step of preventing thermal damage to the epidermis by directing airflow to the irradiated area of the epidermis.

4. A method of treating rheumatoid and psoriatic arthritic inflammation on the body of a subject, the method comprising the steps of:
   providing a radiation source that produces a converging beam with wavelengths having a bandwidth in the range of 640 to 800 nanometers;
   converting the beam;
   filtering all wavelengths outside the wavelength bandwidth while the beam is converging then diverging;
   directing the filtered radiation at the epidermis of the subject adjacent the arthritic inflammation; and
   reducing the arthritic inflammation by maintaining the radiation output at an incident power on the order of between about 40 to 200 milliwatts per square centimeter for a time sufficient to provide an effective treatment but not to exceed 100 joules per square centimeter when the output of the radiation source transilluminates the affected soft tissues.

* * * * *